United States Patent
Jansen et al.

(10) Patent No.: US 9,783,834 B2
(45) Date of Patent: Oct. 10, 2017

(54) DICARBOXYLIC ACID FERMENTATION PROCESS

(75) Inventors: Mickel Leonardus August Jansen, The Hague (NL); Rene Verwaal, Nootdorp (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/388,945

(22) PCT Filed: Aug. 24, 2010

(86) PCT No.: PCT/EP2010/062345
§ 371 (c)(1),
(2), (4) Date: Feb. 3, 2012

(87) PCT Pub. No.: WO2011/023700
PCT Pub. Date: Mar. 3, 2011

(65) Prior Publication Data
US 2012/0135482 A1   May 31, 2012

Related U.S. Application Data

(60) Provisional application No. 61/237,362, filed on Aug. 27, 2009.

(30) Foreign Application Priority Data

Aug. 27, 2009 (EP) ..................................... 09168858

(51) Int. Cl.
C12P 7/46 (2006.01)
C12N 1/18 (2006.01)
C12N 9/88 (2006.01)

(52) U.S. Cl.
CPC ................ *C12P 7/46* (2013.01); *C12N 1/18* (2013.01); *C12N 9/88* (2013.01)

(58) Field of Classification Search
None
See application file for complete search history.

(56) References Cited

U.S. PATENT DOCUMENTS

| | | | |
|---|---|---|---|
| 5,869,301 A * | 2/1999 | Nghiem et al. ............... | 435/136 |
| 2003/0228671 A1 | 12/2003 | Hause et al. | |
| 2011/0081694 A1 | 4/2011 | Verwaal et al. | |

FOREIGN PATENT DOCUMENTS

| | | |
|---|---|---|
| CN | 1688703 A | 10/2005 |
| WO | 03102152 A2 | 12/2003 |
| WO | WO 2007061590 A1 * | 5/2007 |
| WO | WO 2007106524 A2 * | 9/2007 |
| WO | 2008/144626 | 11/2008 |
| WO | 2009/011974 | 1/2009 |
| WO | 2009/065780 | 5/2009 |

OTHER PUBLICATIONS

Pines O, et al. Overexpression of cytosolic malate dehydrogenase (MDH2) causes overproduction of specific organic acids in *Saccharomyces cerevisiae*. Applied Microbiology and Biotechnology. 1997. 48:248-255.*
Battat et al., "Optimization of L-Malic Acid Production by Aspergillus Flavus in a Stirred Fermentor," Biotechnology and Bioengineering, vol. 37, No. 11, pp. 1108-1116, (May 1991).
Abbott et al., "Metabolic Engineering of *Saccharomyces cerevisiae* for Production of Carboxylic Acids: Current Status and Challenges," FEMS Yeast REsearch, Wiley-Blackwell Publishing, vol. 9, No. 8, pp. 1123-1136, (Jun. 29, 2009).
Zelle et al., "Malic Acid Production by *Saccharomyces cerevisiae*: Engineering of Pyruvate Carboxylation, Oxaloacetate Reduction, and Malate Export," Applied and Environmental Microbiology, vol. 74, No. 9, pp. 2766-2777, (May 1, 2008).
Xiaoyan et al., "Studies on the Correlation Between Production of L-Malic Acid and Some Cytosolic Enzymes in the L-Malic Acid Production Strain *Aspergillus* SP. N1-14," Abstract; Database Biosis, Accession No. PREV200100127873, 1 page, (Oct. 2000).
Goldberg et al., "Organic Acids: Old Metabolites, New Themes," Journal of Chemical Technology and Biotechnology, vol. 81, No. 10, pp. 1601-1611, (Oct. 1, 2006).
Kubota et al., "Production of Malic Acid by Baker's Yeast: Fixation of Carbon Dioxide," Journal of Molecular Catalysis B Enzymatic, vol. 48, No. 3-4, p. 113, (Sep. 2007).
International Search Report for PCT/EP2010/062345 Mailed Febr. 22, 2011.

* cited by examiner

*Primary Examiner* — Paul Holland
(74) *Attorney, Agent, or Firm* — McBee Moore Woodward & Vanik IP, LLC; Susan McBee; Chester Moore

(57) ABSTRACT

The present invention relates to a process for producing a dicarboxylic acid, comprising fermenting a recombinant fungal cell in a suitable fermentation medium, in the presence of high carbon dioxide concentrations.

16 Claims, 2 Drawing Sheets

DICARBOXYLIC ACID FERMENTATION PROCESS

CROSS REFERENCE TO RELATED APPLICATIONS

This application is a §371 National Stage Application of PCT/EP2010/062345, filed Aug. 24, 2010, which claims priority to European Patent Application No. 09168858.0; and U.S. Provisional Application No. 61/237,362, filed Aug. 27, 2009.

FIELD OF THE INVENTION

The present invention relates to a process for the production of dicarboxylic acids. In particular, it relates to the production of dicarboxylic acids by fermentation of yeast.

DESCRIPTION OF RELATED ART

Dicarboxylic acids, such as malic acid and succinic acid, are important compounds which are used in the food industry for the preparation and preservation of food, in the medical industry for the formulation of medical products and for other industrial uses, such as monomers for (bio) polymers. Dicarboxylic acids can be produced by petrochemical processes or fermentation based processes, by either bacteria or fungal cells. Bacteria that have been studied for improved succinic acid production are for example *E. coli, Mannheimia* sp., *Actinobacillus* sp. or *Corynebacteria*. A disadvantage of bacterial dicarboxylic acid fermentation processes is that such processes need to be carried out at high pH and neutralizing agents are needed to maintain the pH at a desired value. In addition, neutral pH processes require sterile process conditions, increasing the production costs further.

In contrast to bacteria, fungal cells are able to grow at low pH values and do not require strictly sterile process conditions, making fungal cells an attractive alternative for the production of dicarboxylic acids.

In WO2009/065780 recombinant fungal cells such as yeast and filamentous fungus were developed for the production of dicarboxylic acids, resulting in increased production levels of succinic acid and fumaric acid.

WO2008/144626 shows that the addition of carbon dioxide of up to 10 v/v% increased production levels of malic acid and succinic acid by a recombinant yeast cell, but higher concentrations of carbon dioxide did not further increase dicarboxylic acid production levels.

Despite the improvements made with genetically modified fungal cells for producing dicarboxylic acids, there is a need for further improving dicarboxylic acid production by fungal cells.

SUMMARY

The present invention relates to a process for producing a dicarboxylic acid, comprising fermenting a recombinant fungal cell in a suitable fermentation medium, which comprises a carbon dioxide concentration ranging between 25 and 75 v/v % of total gas present in the fermentation medium and producing the dicarboxylic acid. Surprisingly, it was found that the yield of dicarboxylic acid (g/g sugar) in the process according to the present invention was increased significantly compared to a process comprising carbon dioxide outside of the concentration range of the invention.

Another advantage of the process according to the invention was that the specific productivity (g dicarboxylic acid/g sugar/h) was also increased significantly as compared to a process for the production of dicarboxylic acid comprising carbon dioxide outside of the concentration range of the invention.

DETAILED DESCRIPTION OF A PREFERRED EMBODIMENT

Definitions

Figure 1:
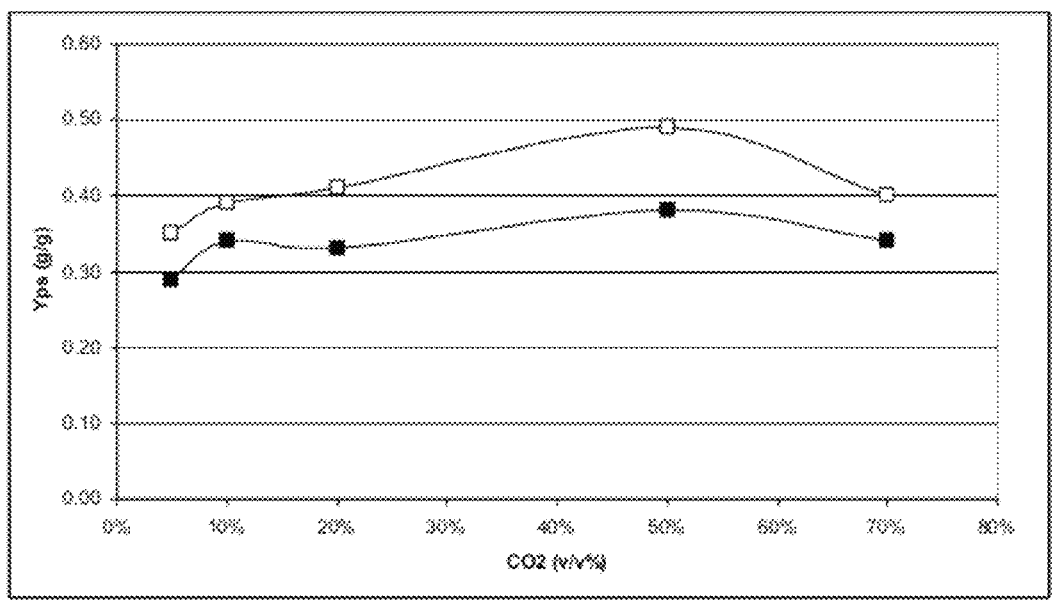
FIGS. 1-2 represent embodiments as described herein.

The terms "dicarboxylic acid" and "dicarboxylate", such as "succinic acid" and "succinate" have the same meaning herein and are used interchangeably, the first being the hydrogenated form of the latter.

The term fermenting or fermentation as used herein refers to the microbial production of compounds such as alcohols or acids from carbohydrates.

A recombinant fungal cell according to the present invention is defined herein as a cell which contains a disruption of a gene or contains, or is transformed or genetically modified with a nucleotide sequence that does not naturally occur in the fungal cell, or it contains additional copy or copies of an endogenous nucleic acid sequence. A wild-type fungal cell is herein defined as the parental cell of the recombinant cell.

Disruption, or deletion or knock-out of a gene means that part of a gene or the entire gene has been removed from a cell, or a gene has been modified such that the gene is not transcribed into the original encoding protein.

The term "homologous" when used to indicate the relation between a given (recombinant) nucleic acid (DNA or RNA), gene or polypeptide molecule and a given host organism or host cell, is understood to mean that in nature the nucleic acid or polypeptide molecule is produced by a host cell or organisms of the same species, preferably of the same variety or strain.

The term "heterologous" when used with respect to a nucleic acid (DNA or RNA) or protein refers to a nucleic acid, gene or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but have been obtained from another cell or synthetically or recombinantly produced.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity and similarity are codified in publicly available computer programs. Preferred computer program methods to determine identity and similarity between two sequences include BLASTP and BLASTN, publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extension 1, Blosum 62 matrix.

There are known methods in the art for overexpression of genes encoding enzymes. A gene encoding an enzyme may be overexpressed by increasing the copy number of the gene coding for the enzyme in the cell, e.g. by integrating additional copies of the gene in the cell's genome, by expressing the gene from a centromeric vector, from an episomal multicopy expression vector or by introducing an (episomal) expression vector that comprises multiple copies of one or more gene(s). Preferably, overexpression of a gene encoding an enzyme according to the invention is achieved with a (strong) constitutive promoter.

Suitable promoters in fungal cells are known to the skilled man in the art. Suitable promotors may be, but are not limited to, TDH1, TDH3, GAL7, GAL10, GAL1, CYC1, HIS3, ADH1, PH05, ADC1, ACT1, TRP1, URA3, LEU2, ENO1, TPI1, AOX1, PGL, GPDA and GAPDH. Other suitable promoters include PDC1, GPD1, PGK1, and TEF1.

A gene encoding an enzyme may be ligated into a nucleic acid construct, for instance a plasmid, such as a low copy plasmid or a high copy plasmid. The fungal cell according to the present invention may comprise a single copy, but preferably comprises multiple copies of a gene, for instance by multiple copies of a nucleotide construct.

A nucleic acid construct may be maintained episomally and thus comprises a sequence for autonomous replication, such as an autonomously replicating sequence and a centromere (Sikorski and Hieter, 1989, Genetics 122, 19-27). A suitable episomal nucleic acid construct may e.g. be based on the yeast 2μ or pKD1 plasmids (Gleer et al., 1991, Biotechnology 9: 968-975), or the AMA plasmids (Fierro et al., 1995, Curr. Genet. 29:482-489). Alternatively, each nucleic acid construct may be integrated in one or more copies into the genome of the fungal cell. Integration into the cell's genome may occur at random by non-homologous recombination but preferably, the nucleic acid construct may be integrated into the cell's genome by homologous recombination as is well known in the art.

In one embodiment the process for producing a dicarboxylic acid, comprising fermenting a recombinant fungal cell in a suitable fermentation medium comprises a carbon dioxide concentration ranging between 25 and 75 v/v %, for example between 35 and 65 v/v %, or between 40 and 60 v/v % of total gas present in the fermentation medium.

The carbon dioxide present in the fermentation medium may be added to the medium in the form of gaseous carbon dioxide in a gas flow, for instance a gas flow comprising carbon dioxide at a concentration between 25 and 75 v/v %. Suitable concentrations of carbon dioxide in a gas flow may range as described herein above.

The carbon dioxide may also be present in the fermentation medium by the addition of carbonate or bicarbonate salt, for instance calcium carbonate or calcium bicarbonate. Usually carbon dioxide is also formed during fermentation of a recombinant fungal cell in the process of the invention.

As used herein the term total gas in the fermentation medium comprises dissolved and not dissolved gas. Total gas in the fermentation medium comprises carbon dioxide and oxygen, and usually further comprises nitrogen and may comprise any gas molecules produced by fermenting the fungal cell, or added to the fermentation medium by e.g. sparging a gas flow through the fermentation medium.

It was found advantageous that total gas in the fermentation comprises oxygen, providing the recombinant fungal cell to generate energy via oxidation. Preferably, the total gas comprises low amounts of oxygen.

Preferably, the process as disclosed herein is carried out under aerobic conditions, preferably under microaerophilic conditions or oxygen limited conditions. Microaerophilic or oxygen limited conditions are reflected in the oxygen uptake rate (OUR). For example, the process described herein comprises supplying oxygen at an oxygen uptake rate lower than 8.0 mmol oxygen/L/hour and above 0.01 mmol oxygen/L/hour.

In one embodiment the OUR is lower than about 6.0 mmol oxygen/L/hour, preferably lower than about 5.0, 4.0, 3.0, or 2.0 mmol oxygen/L/hour, more preferably lower than about 1.0, or 0.5 mmol oxygen/L/hour, preferably above 0.01 mmol oxygen/L/hour. It was found that oxygen-limited conditions resulted in an increased yield of dicarboxylic acid in the process according to the present invention.

In one embodiment the fermentation medium in the process disclosed herein comprises a carbon source, preferably a carbon source selected from the group consisting of glucose, fructose, galactose, xylose, arabinose, sucrose, lactose, maltose, raffinose and glycerol. The fermentation medium usually comprises a nitrogen source such as ammonium or ureum. The fermentation medium may comprise biotin.

In one embodiment in the process for producing a dicarboxylic acid of the present disclosure, a recombinant fungal cell overexpresses a gene encoding a phosphoenol pyruvate (PEP) carboxykinase. Any PEP-carboxykinase catalyzing the reaction from phospoenol pyruvate to oxaloacetate (4.1.1.49) may be suitable for overexpression in a fungal cell. A fungal cell may overexpress a heterologous PEP carboxykinase, such as a PEP carboxykinase derived from *Escherichia coli, Mannheimia* sp., *Actinobacillus* sp., or *Anaerobiospirillum* sp., more preferably *Mannheimia succiniciproducens, Actinobacillus succinogenes*, or *Anaerobiospirillum succiniciproducens*. In one embodiment a gene overexpressing a PEP carboxykinase in a fungal cell in the process herein disclosed is expressed in the cytosol. In one embodiment a fungal cell of the present disclosure overexpresses a gene encoding a PEP-carboxykinase comprising an amino acid sequence that has at least 70, 80, 90, 95, 97, 98, 99 or 100% sequence identity with the amino acid sequence of SEQ ID NO: 6.

It was found advantageous that a recombinant fungal cell overexpresses a PEP-carboxykinase in the process for producing of a dicarboxylic acid in the presence of 25 to 75 v/v % carbon dioxide, since overexpression of PEP carboxykinase resulted in an increased fixation of carbon dioxide, i.e. the conversion of phosphoenol pyruvate (C3) to oxaloacetate (C4), resulting in a higher yield of dicarboxylic acid.

In another embodiment in the process for producing a dicarboxylic acid of the present disclosure a recombinant fungal cell overexpresses a pyruvate carboxylase (PYC), that catalyses the reaction from pyruvate to oxaloacetate (EC 6.4.1.1). Preferably the pyruvate carboxylase is active in the cytosol upon expression of the gene. Preferably, an endogenous or homologous pyruvate carboxylase is overexpressed.

In another embodiment, a recombinant fungal cell in the process for producing a dicarboxylic acid disclosed herein comprises a disruption of a gene encoding an enzyme of the ethanol fermentation pathway. A gene encoding an enzyme of an ethanol fermentation pathway, may be pyruvate decarboxylase (EC 4.1.1.1), catalyzing the reaction from pyruvate to acetaldehyde, or alcohol dehydrogenase (EC 1.1.1.1), catalyzing the reaction from acetaldehyde to ethanol. Preferably, a fungal cell in the process as disclosed herein comprises a disruption of one, two or more genes encoding an alcohol dehydrogenase. In the event the fungal cell is a yeast, e.g. *Saccharomyces cerevisiae*, the *Saccharomyces cerevisiae* preferably comprises a disruption of an alcohol dehydrogenase gene adh1 and/or adh2.

The process for producing a dicarboxylic acid of the present disclosure was found particularly advantageous for cells comprising a disruption of a gene encoding an enzyme of the ethanol fermentation pathway. This resulted in an increase of dicarboxylic acid yield and at the same time cells lacking the ability to produce energy in the form of ATP by ethanol fermentation, were able to fulfill the requirement of ATP formation via oxidation.

In another embodiment, a fungal cell disclosed herein comprises a disruption of a gene encoding a glycerol-3-phosphate dehydrogenase. Disruption of a gene encoding a glycerol-3-phosphate dehydrogenase usually results in a reduced formation of glycerol. In the event the fungal cell is a yeast, such as *Saccharomyces cerevisiae*, the fungal cell preferably comprises a disruption of a gpd1 gene.

In one embodiment the recombinant fungal cell further overexpresses a gene encoding an enzyme selected from the group consisting of a malate dehydrogenase, a fumarase, a (NAD(H)-dependent fumarate reductase, and a dicarboxylic acid transporter protein.

Preferred embodiments of these enzymes are as described herein below.

In one embodiment a fungal cell of the present disclosure further overexpresses a gene encoding a malate dehydrogenase (MDH) active in the cytosol upon expression of the gene. A cytosolic MDH may be any suitable homologous or heterologous malate dehydrogenase, catalyzing the reaction from oxaloacetate to malate (EC 1.1.1.37). Preferably a fungal cell comprises a gene encoding a malate dehydrogenase that has at least 70, 80, 90, 92, 94, 95, 96, 97, 98, 99 or 100% sequence identity with the amino acid sequence of SEQ ID NO: 9.

In another embodiment a fungal cell of the present disclosure further overexpresses a gene encoding a fumarase, that catalyses the reaction from malic acid to fumaric acid (EC 4.2.1.2). A gene encoding fumarase may be derived from any suitable origin, preferably from microbial origin, for instance a yeast such as *Saccharomyces* or a filamentous fungus, such *Rhizopus oryzae*. A fungal cell of the present disclosure may overexpress a nucleotide sequence encoding a fumarase that has at least 70%, or, 80, 90, 92, 94, 95, 96, 97, 98, 99, 100% sequence identity with the amino acid sequence of SEQ ID NO: 8. In one embodiment the enzyme catalysing the conversion of malic acid to fumaric acid is active in the cytosol upon expression of the nucleotide sequence. It was found that cytosolic activity of fumarase resulted in a high productivity of a dicarboxylic acid by the fungal cell.

In another embodiment the fungal cell overexpresses any suitable heterologous or homologous gene encoding a NAD(H)-dependent fumarate reductase, catalyzing the reaction from fumarate to succinate (EC 1.3.1.6). The NADH-dependent fumarate reductase may be a heterologous enzyme, which may be derived from any suitable origin, for instance bacteria, fungi, protozoa or plants. A fungal cell of the present discolsure comprises a heterologous NAD(H)-dependent fumarate reductase, preferably derived from a *Trypanosoma* sp, for instance a *Trypanosoma brucei*. In one embodiment the NAD(H)-dependent fumarate reductase is expressed in the cytosol. The fungal cell may overexpress a gene encoding a NAD(H)-dependent fumarate reductase that has at least 70, 80, 90, 92, 94, 96, 98, or 100% sequence identity with SEQ ID NO:7.

In another embodiment the fungal cell overexpresses a gene encoding a dicarboxylic acid transporter protein, for instance a malic acid transporter protein (MAE). A dicarboxylic acid transporter protein may be a homologous or heterologous protein. A dicarboxylic acid transporter protein may be derived from any suitable organism, for instance from *Schizosaccharomyces pombe*. A fungal cell as disclosed herein may comprise a dicarboxylic acid transporter protein which has at least 70, 80, 85, 90, 95, 99 or 100% sequence identity with SEQ ID NO: 10.

In one embodiment the fungal cell is a yeast or a filamentous fungus, for instance belonging to the genera *Saccharomyces*, *Aspergillus*, *Penicillium*, *Pichia*, *Kluyveromyces*, *Yarrowia*, *Candida*, *Hansenula*, *Humicola*, *Issatchenkia*, *Torulaspora*, *Trichosporon*, *Brettanomyces*, *Rhizopus*, *Zygosaccharomyces*, *Pachysolen* or *Yamadazyma*. The fungal cell may for instance belong to a species *Saccharomyces cervisiae*, *Saccharomyces uvarum*, *Saccharomyces bayanus*, *Aspergillus niger*, *Penicillium chrysogenum*, *Pichia stipidis*, *Kluyveromyces marxianus*, *K. lactis*, *K. thermotolerans*, *Yarrowia lipolytica*, *Candida sonorensis*, *C. glabrata*, *Hansenula polymorpha*, *Issatchenkia orientalis*, *Torulaspora delbrueckii*, *Brettanomyces bruxellensis*, *Rhizopus oryzae* or *Zygosaccharomyces baiffi*. In one embodiment the fungal cell is a yeast, for instance belonging to a *Saccharomyces* sp., preferably a *Saccharomyces cerevisiae*.

Any suitable dicarboxylic acid may be produced in the process as described herein, for instance succinic acid, fumaric acid or malic acid, for instance succinic acid.

The process for the production of a dicarboxylic acid of the present disclosure may be carried out at any suitable pH between 1 and 8. The pH in the fermentation broth may be between 2 and 7, preferably between 3 and 5.

A suitable temperature at which the process of the present disclosure be carried out is between 5 and 60° C., or between 10 and 50° C., for instance between 15 and 45° C., or between 20° C. and 40° C. The skilled man in the art knows the optimal temperatures for fermenting a specific fungal cell.

In another embodiment the process comprises recovering the dicarboxylic acid from the fermentation medium by a suitable method known in the art, for instance by crystallisation, ammonium precipitation or ion exchange technology.

In one embodiment, the dicarboxylic acid that is prepared in the process according to the present invention is further converted into a pharmaceutical, cosmetic, food, feed, or polyester polymer. Succinic acid may for instance be further converted into a polymer, such as polybutylene succinate (PBS).

In another embodiment the process according to present invention is carried out on an industrial scale. Industrial is herein defined as a fermentation process that is carried out in a volume of at least 10 liters, preferably at least 100 liters, preferably at least 1 cubic metre ($m^3$), more preferably at least 10, 100, or 1000 cubic metres ($m^3$), usually below 10,000 cubic metres ($m^3$).

The invention also relates to a process for producing a dicarboxylic acid comprising fermenting a recombinant fungal cell in a suitable fermentation medium, wherein carbon dioxide in a concentration of 20 to 80 v/v % of total gas present in the fermentation medium is used to increase dicarboxylic acid production.

FIGURES

FIG. 1. Effect of the $CO_2$ concentration (v/v %) on the dicarboxylic acid yield ($Y_{ps}$) after 90 h fermentation of yeast SUC-200 at pH 5. Closed square: Yield of succinic acid ($Y_{ps\ SA}$); Open square: Yield of succinic acid+malic acid ($Y_{ps\ SA+MA}$).

Figure 2:
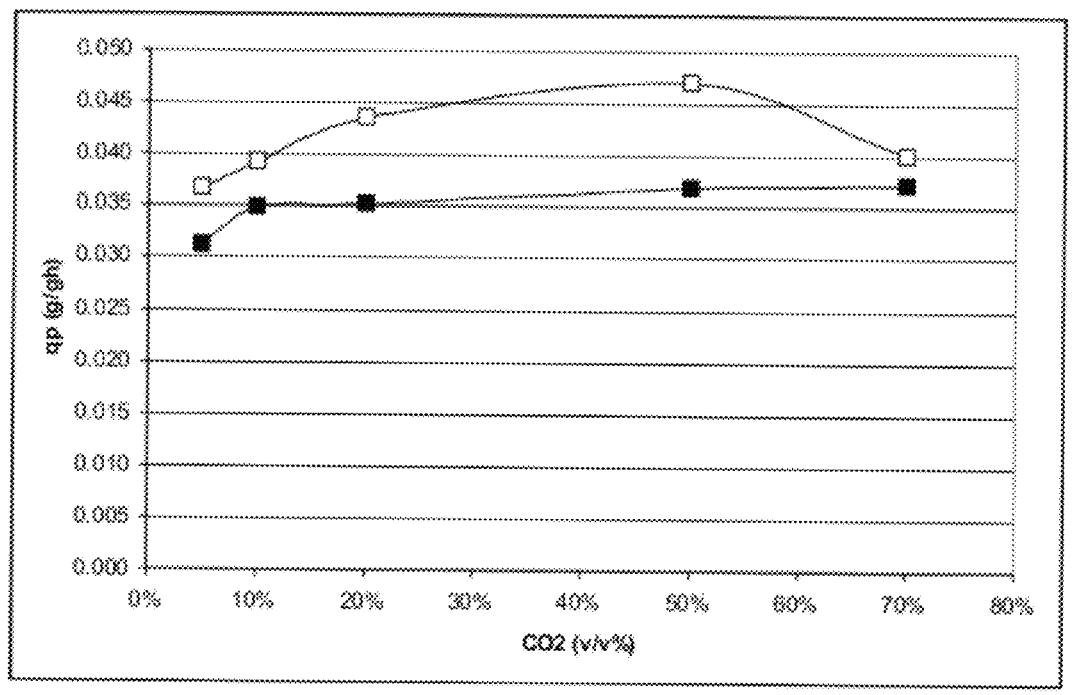

FIG. 2. Effect of the $CO_2$ concentration (v/v %) on the specific dicarboxylic acid productivity ($q_p$) after 90 h fermentation of yeast SUC-200 at pH 5. Closed square: Productivity of succinic acid ($q_{p\ SA}$); Open square: Productivity of succinic acid+malic acid ($q_{p\ SA+MA}$).

EXAMPLES

Example 1

Dicarboxylic Acid Production by Saccharomyces cerevisiae 1.1. Construction Yeast Strain
1.1.1. Construction of Expression Constructs Expression construct pGBS414PPK-3 was created after a BamHI/NotI restriction of the S. cerevisiae expression vector pRS414 (Sirkoski R. S. and Hieter P, Genetics, 1989, 122(1):19-27) and subsequently ligating in this vector a BamHI/NotI restriction fragment consisting of the phosphoenolpyruvate carboxykinase (origin Actinobacillus succinogenes) synthetic gene construct (SEQ ID NO: 1). The ligation mix was used for transformation of E. coli TOP10 (Invitrogen) resulting in the yeast expression construct pGBS414PPK-1. Subsequently, pGBK414PPK-1 was restricted with AscI and NotI. To create pGBS414PPK-3, an AscI/NotI restriction fragment consisting of glycosomal fumarate reductase from T. brucei (FRDg) synthetic gene construct (SEQ ID NO: 2) was ligated into the restricted pGBS414PPK-1 vector. The ligation mix was used for transformation of E. coli TOP10 (Invitrogen) resulting in the yeast expression construct pGBS414PPK-3.

The expression construct pGBS415FUM-3 was created after a BamHI/NotI restriction of the S. cerevisiae expression vector pRS415 (Sirkoski R. S. and Hieter P, Genetics, 1989, 122(1):19-27) and subsequently ligating in this vector a BamHI/NotI restriction fragment consisting of the fumarase (origin Rhizopus oryzae) synthetic gene construct (SEQ ID NO: 3). The ligation mix was used for transformation of E. coli TOP10 (Invitrogen) resulting in the yeast expression construct pGBS415FUM-1. Subsequently, pGBK415FUM-1 was restricted with AscI and NotI. To create pGBS415FUM-3, an AscI/NotI restriction fragment consisting of peroxisomal malate dehydrogenase from S. cerevisiae (MDH3) synthetic gene construct (SEQ ID NO: 4) was ligated into the restricted pGBS415FUM-1 vector. The ligation mix was used for transformation of E. coli TOP10 (Invitrogen) resulting in the yeast expression construct pGBS415FUM-3.

The expression construct pGBS416MAE-1 was created after a BamHI/NotI restriction of the S. cerevisiae expression vector pRS416 (Sirkoski R. S. and Hieter P, Genetics, 1989, 122(1):19-27) and subsequently ligating in this vector a BamHI/NotI restriction fragment consisting of the Schizosaccharomyces pombe malate transporter synthetic gene construct (SEQ ID NO: 5). The ligation mix was used for transformation of E. coli TOP10 (Invitrogen) resulting in the yeast expression construct pGBS416MAE-1.

1.1.2. Construction S. cerevisiae Strain

Plasmids pGBS414PPK-3, pGBS415FUM-3 and pGBS416MAE-1 (described under 1.1.1) were transformed by electroporation into S. cerevisiae strain RWB064 (MATA ura3-52 leu2-112 trp1-289 adh1::lox adh2::lox gpd1::Kan-lox) to create strain SUC-200, overexpressing PCKa, MDH3, FUMR, FRDg and SpMAE1. All genes were codon pair optimized for expression in S. cerevisiae according to WO2008/000632.

1.2. Dicarboxylic Acid Fermentation
1.2.1. Fermentation Conditions

The yeast strain SUC-200 as described under paragraph 1.1. was cultivated in shake-flask (2×300 ml) for 3 days at 30° C. and 220 rpm. The medium was based on Verduyn (Verduyn et. al., 1992, Yeast 8, 501-517), but modifications in carbon and nitrogen source were made as shown in Table 1 and 2.

TABLE 1

Preculture shake flask medium composition.

| Raw material | Formula | Concentration (g/l) |
|---|---|---|
| Galactose | $C_6H_{12}O_6 \cdot H_2O$ | 20.0 |
| Urea | $(NH_2)_2CO$ | 2.3 |
| Potassium dihydrogen phosphate | $KH_2PO_4$ | 3.0 |
| Magnesium sulphate | $MgSO_4 \cdot 7H_2O$ | 0.5 |
| Trace element solution[a] | | 1 |
| Vitamin solution[b] | | 1 |

| Component | Formula | Concentration (g/kg) |
|---|---|---|
| Biotin (D-) | $C_{10}H_{16}N_2O_3S$ | 0.05 |
| Ca D(+) panthothenate | $C_{18}H_{32}CaN_2O_{10}$ | 1.00 |
| Nicotinic acid | $C_6H_5NO_2$ | 1.00 |
| Myo-inositol | $C_6H_{12}O_6$ | 25.00 |
| Thiamine chloride hydrochloride | $C_{12}H_{18}Cl_2N_4OS \cdot xH_2O$ | 1.00 |
| Pyridoxol hydrochloride | $C_8H_{12}ClNO_3$ | 1.00 |
| p-aminobenzoic acid | $C_7H_7NO_2$ | 0.20 |
| EDTA | $C_{10}H_{14}N_2Na_2O_8 \cdot 2H_2O$ | 15.00 |
| Zincsulphate•7H2O | $ZnSO_4 \cdot 7H_2O$ | 4.50 |
| Manganesechloride•2H2O | $MnCl_2 \cdot 2H_2O$ | 0.84 |
| Cobalt (II) chloride•6H2O | $CoCl_2 \cdot 6H_2O$ | 0.30 |
| Cupper (II) sulphate•5H2O | $CuSO_4 \cdot 5H_2O$ | 0.30 |
| Sodium molybdenum•2H2O | $Na_2MoO_4 \cdot 2H_2O$ | 0.40 |
| Calciumchloride•2H2O | $CaCl_2 \cdot 2H_2O$ | 4.50 |
| Ironsulphate•7H2O | $FeSO_4 \cdot 7H_2O$ | 3.00 |
| Boric acid | $H_3BO_3$ | 1.00 |
| Potassium iodide | $KI$ | 0.10 |

[a]Vitamin solution
[b]Trace elements solution

Subsequently, the contents of the shake-flasks were transferred to a 10 L fermenter (Startweight 6 kg), which contained the following medium:

TABLE 2

Main fermentation medium composition.

| Raw material | | Concentration (g/l) |
|---|---|---|
| Ammonium sulphate | $(NH_4)_2SO_4$ | 2.5 |
| Potassium dihydrogen phosphate | $KH_2PO_4$ | 3.0 |
| Magnesium sulphate | $MgSO_4 \cdot 7H_2O$ | 0.5 |
| Trace element solution | | 1 |
| Vitamin solution | | 1 |

The pH during the fermentation was controlled at 5.0 by addition of 6 N KOH. The temperature was controlled at 30° C. Glucose concentration was kept limited (<1 g/l) by controlled feed to the fermenter. Oxygen uptake rate (OUR)

was controlled at 5 mmol/kg/h during the fermentation, which resulted in oxygen limitation. A total gasflow of 0.33 vvm was applied, with varying percentages of $CO_2$ in the gas mixture. During the cultivation of 90 hours growth occurred to a typical biomass concentration of 8 g/L.

1.2.2. NMR Analyses

Dicarboxylic acid concentrations in the fermentation supernatant were determined by means of NMR spectroscopy.

3 ml broth was centrifuged for 10 min at 4500×g. Approximately 500 microlitres of supernatant were accurately weighed to a headspace vial. To each sample 0.5 ml of pen buffer C-2696 (containing 5.62 mg/ml maleic acid) was added. The samples were capped and cooked for about 10 minutes in a water bath (and in oil bath in the control sample CF292706-11 and CF292706-12) at 100° C. The samples were lyophilized, the residue was dissolved in 1 ml $D_2O$.

The spectra were recorded at a proton frequency of Bruker DRX 360 MHz at a probe temperature of 300 K. The quantitative measurements were performed with pulse program zg, excitation pulse from 30-90 degrees and a relaxation delay of 40 s.

FIG. 1 shows that a $CO_2$ concentration increasing to about 50 v/v % resulted in an increased yield $Y_{ps}$ (g/g) of succinic acid and increased yield of malic acid (MA) plus succinic acid (SA) of about 10 to 30% as compared to a $CO_2$ concentration of 10 v/v %. An overall yield of SA+MA of 0.49 g/g was achieved when applying 50 v/v % $CO_2$, whereas 10 v/v % $CO_2$ resulted in a yield of 0.36 g/g SA+MA. The yield of SA+MA without the addition of $CO_2$ during the fermentation was 0.23 g/g.

Likewise the specific productivity $q_p$ (g/g/h) increased at higher $CO_2$ concentrations (FIG. 2). A concentration of 50 v/v % $CO_2$ resulted in an increased specific productivity of SA+MA ($q_{p\ SA+MA}$) of 0.047 g/g/h compared to 0.039 g/g/h using 10 v/v % $CO_2$.

CONCLUSION

The results show that carbon dioxide concentrations of between 25 and 75 v/v % had a positive effect on the yield and specific productivity of a dicarboxylic acid (succinic acid and malic acid) by a recombinant fungal cell, such as a recombinant *Saccharomyces cerevisiae*.

The invention claimed is:

1. A process for producing a dicarboxylic acid selected from the group consisting of succinic acid, fumaric acid, and malic acid, comprising:
fermenting a recombinant yeast in a fermentation medium comprising a carbon dioxide concentration ranging from 25 to 75 v/v % of total gas present in said fermentation medium,
and producing said dicarboxylic acid.

2. The process of claim 1, wherein said recombinant yeast overexpresses, relative to a non-recombinant yeast, a gene encoding a phosphoenol pyruvate carboxykinase.

3. The process of claim 1, wherein said recombinant yeast comprises a disruption of a gene encoding an enzyme of the ethanol fermentation pathway.

4. The process of claim 3, wherein said enzyme is an alcohol dehydrogenase.

5. The process of claim 1, wherein said recombinant yeast overexpresses, relative to a non-recombinant yeast, a gene encoding an enzyme selected from the group consisting of a malate dehydrogenase, a fumarase, a NAD(H)-dependent fumarate reductase, and a dicarboxylic acid transporter protein.

6. The process of claim 1, wherein said yeast is *Saccharomyces* sp.

7. The process of claim 1, wherein said dicarboxylic acid is succinic acid.

8. The process of claim 1, wherein said fermentation medium has a pH value of from 2 to 6.

9. The process of claim 1, further comprising recovering said dicarboxylic acid.

10. The process of claim 1, wherein said process is carried out in a volume of at least 10 liters.

11. The process of claim 1, wherein said dicarboxylic acid is converted into a pharmaceutical, cosmetic, food, feed or polyester polymer.

12. The process of claim 1, wherein said yeast yeast is *Saccharomyces cerevisiae*.

13. The process of claim 1, wherein the yield of dicarboxylic acid (g/g sugar) is increased compared to said process when said fermentation medium comprises a carbon dioxide concentration below 25 or above 75 v/v % of total gas present in said fermentation medium.

14. The process of claim 1, wherein the specific productivity (g dicarboxylic acid/ g sugar/ h) is increased compared to said process when said fermentation medium comprises a carbon dioxide concentration below 25 or above 75 v/v % of total gas present in said fermentation medium.

15. The process of claim 1, wherein said fermenting is carried out under microaerophilic conditions.

16. The process of claim 15, comprising supplying oxygen at an oxygen uptake rate lower than 8.0 mmol oxygen/ L/hour and above 0.01 mmol oxygen/L/hour.

* * * * *

SEQUENCE LISTING

```
<160> NUMBER OF SEQ ID NOS: 10

<210> SEQ ID NO 1
<211> LENGTH: 3148
<212> TYPE: DNA
<213> ORGANISM: Artificial Sequence
<220> FEATURE:
<223> OTHER INFORMATION: Synthetic construct TDH1p-PCKa-TDH1t for
      expression in S. cerevisiae

<400> SEQUENCE: 1
ggatcccttc cctttacag tgcttcggaa aagcacagcg ttgtccaagg gaacaatttt       60
tcttcaagtt aatgcataag aaatatcttt ttttatgttt agctaagtaa aagcagcttg      120
gagtaaaaaa aaaaatgagt aaatttctcg atggattagt ttctcacagg taacataaca     180
aaaaccaaga aaagcccgct tctgaaaact acagttgact tgtatgctaa agggccagac     240
taatgggagg agaaaaagaa acgaatgtat atgctcattt acactctata tcaccatatg     300
gaggataagt tgggctgagc ttctgatcca atttattcta tccattagtt gctgatatgt     360
cccaccagcc aacacttgat agtatctact cgccattcac ttccagcagc gccagtaggg     420
ttgttgagct tagtaaaaat gtgcgcacca caagcctaca tgactccacg tcacatgaaa     480
ccacaccgtg gggccttgtt gcgctaggaa taggatatgc gacgaagacg cttctgctta     540
gtaaccacac cacatttca ggggtcgat ctgcttgctt cctttactgt cacgagcggc       600
ccataatcgc gctttttttt taaaggcgc gagacagcaa acaggaagct cgggtttcaa      660
ccttcggagt ggtcgcagat ctggagactg gatctttaca atacagtaag gcaagccacc     720
atctgcttct taggtgcatg cgacggtatc cacgtgcaga acaacatagt ctgaagaagg     780
gggggaggag catgttcatt ctctgtagca gtaagagctt ggtgataatg accaaaactg     840
gagtctcgaa atcatataaa tagacaatat attttcacac aatgagattt gtagtacagt     900
tctattctct ctcttgcata aataagaaat tcatcaagaa cttggtttga tatttcacca     960
acacacacaa aaaacagtac ttcactaaat ttacacacaa aacaaaatga ccgatttgaa    1020
ccaattgact caagaattgg gtgctttggg tattcacgat gtccaagaag ttgtctacaa    1080
cccatcttac gaattgttgt ttgctgaaga aaccaagcca ggtttggaag gttacgaaaa    1140
```

```
gggtactgtt accaaccaag gtgctgttgc tgtcaacacc ggtatcttca ccggtcgttc    1200
tccaaaggac aaatacattg tcttggatga caagaccaag acactgtct ggtggacttc    1260 tgaaaggtc aagaacgaca acaaaccaat gtcccaagac acttggaact ctttaaaggg    1320
tttagtcgct gaccaattgt ctggtaagag attattcgtt gtcgatgctt tctgtggtgc    1380
caacaaggac accagattag ctgtcagagt tgtcactgaa gttgcttggc aagctcactt    1440
cgttaccaac atgttcatca gaccatctgc tgaagaattg aaaggtttca agccagattt    1500
cgttgtcatg aacggtgcca atgtaccaa cccaaactgg aaggaacaag gtttgaactc    1560
tgaaaacttt gttgctttca acatcactga aggtgttcaa ttgattggtg gtacctggta    1620
cggtggtgaa atgaagaagg gtatgttctc catgatgaac tacttcttgc cattgagagg    1680
tattgcttcc atgcactgtt ctgccaatgt cggtaaggac ggtgacactg ccatcttctt    1740
cggtctatcc ggtaccggta agaccacttt gtccactgac ccaaagagac aattgattgg    1800
tgatgacgaa cacggttggg atgacgaagg tgttttcaac tttgaaggtg gttgttacgc    1860
caagaccatc aacttatctg ctgaaaatga accagatatc tacggtgcca tcaagcgtga    1920
cgctctattg gaaaacgttg ttgttttgga caatggtgac gtcgattatg ctgacggttc    1980
caagactgaa aacaccagag tttcttaccc aatctaccat attcaaaaca ttgtcaagcc    2040
agtttccaag gctggtccag ctaccaaagt tatcttcttg tctgctgatg ctttcggtgt    2100
tttgcctcct gtttccaagt tgactccaga acaaaccaag tactacttct tgtctggttt    2160
caccgccaag ttggctggta ctgaaagagg tatcactgaa ccaactccaa ctttctctgc    2220
ttgtttcggt gctgcctttt tgtctttgca cccaactcaa tacgctgaag ttttggtcaa    2280
gagaatgcaa gaatctggtg ctgaagctta cttggtcaac actggttgga acggtaccgg    2340
taagagaatc tccatcaaag ataccagagg tatcatcgat gccatcttgg atggttccat    2400
tgacaaggct gaaatgggtt cttttgccaat tttcgatttc tccattccaa aggctttgcc    2460
aggtgtcaac ccagccatct tagacccaag agacacctac gctgacaaag ctcaatggga    2520
agaaaaggct caagacttgg ctggtagatt cgtcaagaac ttcgaaaaat acactggtac    2580
tgctgaaggt caagctttgg ttgctgctgg tccaaaggcc taaggcccgg gcataaagca    2640
atcttgatga ggataatgat tttttttttga atatacataa atactaccgt ttttctgcta    2700 gatttgtga agacgtaaat aagtacatat tactttttaa gccaagacaa gattaagcat    2760
taactttacc cttttctctt ctaagtttca atactagtta tcactgttta aaagttatgg    2820
cgagaacgtc ggcggttaaa atatattacc ctgaacgtgg tgaattgaag ttctaggatg    2880
gtttaaagat ttttcctttt tgggaaataa gtaaacaata tattgctgcc tttgcaaaac    2940
gcacataccc acaatatgtg actattggca aagaacgcat tatcctttga agaggtggat    3000
actgatacta agagagtctc tattccggct ccactttag tccagagatt acttgtcttc    3060
ttacgtatca gaacaagaaa gcatttccaa agtaattgca tttgcccttg agcagtatat    3120
atatactaag aaggcgcgcc gcggccgc                                       3148
```

<210> SEQ ID NO 2
<211> LENGTH: 4959
<212> TYPE: DNA
<213> ORGANISM: Artificial Sequence
<220> FEATURE:
<223> OTHER INFORMATION: Synthetic construct TDH3p-FRDg-TDH3t for
      expression in S. cerevisiae

<400> SEQUENCE: 2

```
ggatccggcg cgccctattt tcgaggacct tgtcaccttg agcccaagag agccaagatt    60
taaattttcc tatgacttga tgcaaattcc caaagctaat aacatgcaag acacgtacgg   120
tcaagaagac atatttgacc tcttaacagg ttcagacgcg actgcctcat cagtaagacc   180
cgttgaaaag aacttacctg aaaaaaacga atatatacta gcgttgaatg ttagcgtcaa   240
caacaagaag tttaatgacg cggaggccaa ggcaaaaaga ttccttgatt acgtaaggga   300
gttagaatca ttttgaataa aaaacacgct ttttcagttc gagtttatca ttatcaatac   360
tgccatttca aagaatacgt aaataattaa tagtagtgat tttcctaact ttatttagtc   420
aaaaaattag cctttttaatt ctgctgtaac ccgtacatgc ccaaaatagg gggcgggtta   480
cacagaatat ataacatcgt aggtgtctgg gtgaacagtt tattcctggc atccactaaa   540
tataatggag cccgcttttt aagctggcat ccagaaaaaa aaagaatccc agcaccaaaa   600
tattgttttc ttcaccaacc atcagttcat aggtccattc tcttagcgca actacagaga   660
acagggcac aaacaggcaa aaacgggca caacctcaat ggagtgatgc aacctgcctg    720
gagtaaatga tgacacaagg caattgaccc acgcatgtat ctatctcatt ttcttacacc   780
ttctattacc ttctgctctc tctgatttgg aaaaagctga aaaaaaaggt tgaaaccagt   840
tccctgaaat tattcccta cttgactaat aagtatataa agacggtagg tattgattgt    900
aattctgtaa atctatttct taaacttctt aaattctact tttatagtta gtctttttt   960
tagttttaaa acaccaagaa cttagtttcg aataaacaca cataaacaaa caaatggtt  1020
gatggtagat cttctgcttc cattgttgcc gttgacccag aaagagctgc cagagaaaga  1080
gatgctgctg ccagagcttt gttgcaagac tctccattgc acaccaccat gcaatacgct  1140
acctctggtt tggaattgac tgttccatac gctttgaagg ttgttgcttc tgctgacact  1200
ttcgacagag ccaaggaagt tgctgatgaa gtcttgagat gtgcctggca attggctgac  1260
accgttttga actcttttcaa cccaaactct gaagtctctt tagtcggtag attaccagtc  1320
ggtcaaaagc atcaaatgtc tgctccattg aaacgtgtca tggcttgttg tcaaagagtc  1380
tacaactcct ctgctggttg tttcgaccca tccactgctc cagttgccaa ggctttgaga  1440
gaaattgctt tgggtaagga agaaacaat gcttgtttgg aagctttgac tcaagcttgt  1500
accttgccaa actcttcgt cattgatttc gaagctggta ctatctccag aaagcacgaa  1560
cacgcttctt tggatttggg tggtgtttcc aagggttaca tcgtcgatta cgtcattgac  1620
aacatcaatg ctgctggttt ccaaaacgtt ttctttgact ggggtggtga ctgtcgtgcc  1680
tccggtatga acgccagaaa cactccatgg gttgtcggta tcactagacc tccttccttg  1740
gacatgttgc caaaccctcc aaaggaagct tcttacatct ccgtcatctc tttggacaat  1800
gaagctttgg ctacctctgg tgattacgaa aacttgatct acactgctga cgataaacca  1860
ttgacctgta cctacgattg gaaaggtaag gaattgatga agccatctca atccaatatc  1920
gctcaagttt ccgtcaagtg ttactctgcc atgtacgctg acgctttggc taccgcttgt  1980
ttcatcaagc gtgacccagc caaggtcaga caattgttgg atggttggag atacgttaga  2040
gacaccgtca gagattaccg tgtctacgtc agagaaaacg aaagagttgc caagatgttc  2100
gaaattgcca ctgaagatgc tgaaatgaga agagaagaa tttccaacac tttaccagct  2160
cgtgtcattg ttgttggtgg tggtttggct ggtttgtccg ctgccattga agctgctggt  2220
tgtggtgctc aagttgtttt gatggaaaag gaagccaagt ggggtggtaa ctctgccaag  2280
gctacctctg gtatcaacgg ttggggtact agagctcaag ctaaggcttc cattgtcgat  2340
```

```
ggtggtaagt acttcgaaag agatacctac aagtctggta tcggtggtaa caccgatcca    2400
gctttggtta agactttgtc catgaaatct gctgacgcta tcggttggtt gacttctcta    2460
ggtgttccat tgactgtttt gtcccaatta ggtggtcact ccagaaagag aactcacaga    2520
gctccagaca agaaggatgg tactccattg ccaattggtt tcaccatcat gaaaacttta    2580
gaagatcatg ttagaggtaa cttgtccggt agaatcacca tcatggaaaa ctgttccgtt    2640
acctctttgt tgtctgaaac caaggaaaga ccagacggta ccaagcaaat cagagttacc    2700
ggtgtcgaat tcactcaagc tggttctggt aagaccacca ttttggctga tgctgttatc    2760
ttggccaccg tggtttctc caacgacaag actgctgatt ctttgttgag agaacatgcc    2820
ccacacttgg ttaacttccc aaccaccaac ggtccatggg ctactggtga tggtgtcaag    2880
ttggctcaaa gattaggtgc tcaattggtc gatatggaca aggttcaatt gcacccaact    2940
ggtttgatca acccaaagga cccagccaac ccaaccaaat tcttgggtcc agaagctcta    3000
agaggttctg gtggtgtttt gttgaacaaa caaggtaaga gatttgtcaa cgaattggat    3060
ttgagatctg ttgtttccaa ggccatcatg aacaaggtg ctgaataccc aggttctggt    3120
ggttccatgt tgcttactg tgtcttgaac gctgctgctc aaaaattgtt tggtgtttcc    3180
tctcacgaat tctactggaa gaagatgggt ttgttcgtca aggctgacac catgagagac    3240
ttggctgctt tgattggttg tccagttgaa tccgttcaac aaactttaga agaatacgaa    3300
agattatcca tctctcaaag atcttgtcca attaccagaa aatctgttta cccatgtgtt    3360
ttgggtacca aggtccata ctatgtcgcc tttgtcactc catctatcca ctacaccatg    3420
ggtggttgtt tgatttctcc atctgctgaa atccaaatga gaacacttc ttccagagct    3480 ccattgtccc actccaaccc aatcttgggt ttattcggtg ctggtgaagt caccggtggt    3540
gtccacggtg gtaacagatt aggtggtaac tctttgttgg aatgtgttgt tttcggtaga    3600
attgccggtg acagagcttc taccatttg caaagaaagt cctctgcttt gtctttcaag    3660
gtctggacca ctgttgtttt gagagaagtc agagaaggtg gtgtctacgg tgctggttcc    3720
cgtgtcttga gattcaactt accaggtgct ctacaaagat ctggtctatc cttgggtcaa    3780
ttcattgcca tcagaggtga ctgggacggt caacaattga ttggttacta ctctccaatc    3840
actttgccag acgatttggg tatgattgac attttggcca gatctgacaa gggtacttta    3900
cgtgaatgga tctctgcttt ggaaccaggt gacgctgtcg aaatgaaggc ttgtggtggt    3960
ttggtcatcg aaagaagatt atctgacaag cacttcgttt tcatgggtca cattatcaac    4020
aagctatgtt tgattgctgg tggtaccggt gttgctccaa tgttgcaaat catcaaggcc    4080
gctttcatga agccattcat cgacactttg gaatccgtcc acttgatcta cgctgctgaa    4140
gatgtcactg aattgactta cagagaagtt ttggaagaac gtcgtcgtga atccagaggt    4200
aaattcaaga aaactttcgt tttgaacaga cctcctccat tatggactga cggtgtcggt    4260
ttcatcgacc gtggtatctt gaccaaccac gttcaaccac catctgacaa cttattggtt    4320
gccatctgtg gtccaccagt tatgcaaaga attgtcaagg ccactttaaa gactttaggt    4380
tacaacatga acttggtcag aaccgttgac gaaactgaac catctggaag ttaaggcccg    4440
ggcgtgaatt tactttaaat cttgcattta aataaatttt cttttatag ctttatgact    4500 tagtttcaat ttatatacta ttttaatgac attttcgatt cattgattga aagctttgtg    4560
ttttttcttg atgcgctatt gcattgttct tgtcttttc gccacatgta atatctgtag    4620
tagatacctg atacattgtg gatgctgagt gaaattttag ttaataatgg aggcgctctt    4680 aataatttg gggatattgg cttttttttt taaagtttac aaatgaattt tttccgccag    4740
```

-continued

| | |
|---|---|
| gataacgatt ctgaagttac tcttagcgtt cctatcggta cagccatcaa atcatgccta | 4800 |
| taaatcatgc ctatatttgc gtgcagtcag tatcatctac atgaaaaaaa ctcccgcaat | 4860 |
| ttcttataga atacgttgaa aattaaatgt acgcgccaag ataagataac atatatctag | 4920 |
| atgcagtaat atacacagat tccggccggc cgcggccgc | 4959 |

<210> SEQ ID NO 3
<211> LENGTH: 2950
<212> TYPE: DNA
<213> ORGANISM: Artificial Sequence
<220> FEATURE:
<223> OTHER INFORMATION: Synthetic construct TDH1p-FUMR-TDH1t for
      expression in S. cerevisiae

<400> SEQUENCE: 3

| | |
|---|---|
| ggatcccttc cctttacag tgcttcggaa aagcacagcg ttgtccaagg gaacaatttt | 60 |
| tcttcaagtt aatgcataag aaatatcttt ttttatgttt agctaagtaa aagcagcttg | 120 |
| gagtaaaaaa aaaaatgagt aaatttctcg atggattagt ttctcacagg taacataaca | 180 |
| aaaaccaaga aaagcccgct tctgaaaact acagttgact tgtatgctaa agggccagac | 240 |
| taatgggagg agaaaaagaa acgaatgtat atgctcattt acactctata tcaccatatg | 300 |
| gaggataagt tgggctgagc ttctgatcca atttattcta tccattagtt gctgatatgt | 360 |
| cccaccagcc aacacttgat agtatctact cgccattcac ttccagcagc gccagtaggg | 420 |
| ttgttgagct tagtaaaaat gtgcgcacca caagcctaca tgactccacg tcacatgaaa | 480 |
| ccacaccgtg gggccttgtt gcgctaggaa taggatatgc gacgaagacg cttctgctta | 540 |
| gtaaccacac cacattttca gggggtcgat ctgcttgctt cctttactgt cacgagcggc | 600 |
| ccataatcgc gctttttttt taaaaggcgc gagacagcaa acaggaagct cgggtttcaa | 660 |
| ccttcggagt ggtcgcagat ctggagactg atctttaca atacagtaag gcaagccacc | 720 |
| atctgcttct taggtgcatg cgacggtatc cacgtgcaga acaacatagt ctgaagaagg | 780 |
| gggggaggag catgttcatt ctctgtagca gtaagagctt ggtgataatg accaaaactg | 840 |
| gagtctcgaa atcatataaa tagacaatat attttcacac aatgagattt gtagtacagt | 900 |
| tctattctct ctcttgcata aataagaaat tcatcaagaa cttggtttga tatttcacca | 960 |
| acacacacaa aaaacagtac ttcactaaat ttacacacaa aacaaaatgt cctctgcttc | 1020 |
| tgctgctttg caaaaattca gagctgaaag agataccttc ggtgacttgc aagttccagc | 1080 |
| tgaccgttac tggggtgctc aaactcaaag atctttgcaa aactttgaca ttggtggtcc | 1140 |
| aactgaaaga atgccagaac cattaatcag agctttcggt gttttgaaga aggctgctgc | 1200 |
| caccgtcaac atgacctacg gtttggaccc aaaggttggt gaagccatcc aaaaggctgc | 1260 |
| tgacgaagtt atcgatggtt ctttgattga ccatttccca ttggttgtct ggcaaaccgg | 1320 |
| ttctggtact caaaccaaga tgaacgtcaa tgaagtcatc tccaacagag ccattgaatt | 1380 |
| gttgggtggt gaattaggtt ccaaggctcc agtccaccca aacgatcatg tcaacatgtc | 1440 |
| tcaatcttcc aacgacactt tcccaactgc catgcacgtt gctgccgttg ttgaaattca | 1500 |
| cggtagattg attccagctt tgaccacttt gagagatgct ttgcaagcca atctgctga | 1560 |
| attcgaacac atcatcaaga ttggtagaac ccacttgcaa gatgctaccc cattgacttt | 1620 |
| aggtcaagaa ttctccggtt acactcaaca attgaccttac ggtattgctc gtgttcaagg | 1680 |
| tactttggaa agattataca acttggctca aggtggtact gctgtcggta ctggtttgaa | 1740 |
| caccagaaag ggtttcgatg ccaaggttgc tgaagccatt gcttccatca ctggtttacc | 1800 |

-continued

```
attcaagacc gctccaaaca aattcgaagc tttggctgct cacgacgctt tggttgaagc    1860
tcacggtgct tgaacaccg ttgcttgttc tttgatgaag attgccaacg atatccgtta    1920
cttgggttct ggtccaagat gtggtttagg tgaattgtct ctaccagaaa acgaaccagg    1980
ttcttccatc atgccaggta aggtcaaccc aactcaatgt gaagctatga ccatggtttg    2040
tgctcaagtc atgggtaaca acactgccat ctctgttgct ggttccaacg gtcaattcga    2100
attgaatgtc tttaaaccag tcatgatcaa gaacttgatc caatccatca gattaatctc    2160
tgacgcttcc atctctttca ccaagaactg tgttgtcggt attgaagcta acgaaaagaa    2220
gatctcctcc atcatgaacg aatctttgat gttggtcact gctttgaacc ctcacattgg    2280
ttacgacaag gctgccaagt gtgccaagaa ggctcacaag gaaggtacca ctttgaaaga    2340
agctgctcta tctttgggtt acttgacctc tgaagaattc gaccaatggg ttagacctga    2400
ggacatgatt tctgccaagg attaaggccc gggcataaag caatcttgat gaggataatg    2460
attttttttt gaatatacat aaatactacc gttttttctgc tagattttgt gaagacgtaa    2520
ataagtacat attactttt aagccaagac aagattaagc attaacttta ccctttttctc    2580 ttctaagttt caatactagt tatcactgtt taaaagttat ggcgagaacg tcggcggtta    2640
aaatatatta ccctgaacgt ggtgaattga agttctagga tggtttaaag attttttcctt    2700 tttgggaaat aagtaaacaa tatattgctg cctttgcaaa acgcacatac ccacaatatg    2760
tgactattgg caagaacgc attatccttt gaagaggtgg atactgatac taagagagtc    2820
tctattccgg ctccactttt agtccagaga ttacttgtct tcttacgtat cagaacaaga    2880
aagcatttcc aaagtaattg catttgccct tgagcagtat atatatacta agaaggcgcg    2940
ccgcggccgc                                                           2950

<210> SEQ ID NO 4
<211> LENGTH: 1966
<212> TYPE: DNA
<213> ORGANISM: Artificial Sequence
<220> FEATURE:
<223> OTHER INFORMATION: Synthetic construct TDH3p-MDH3-TDH3t for
      expression in S. cerevisiae

<400> SEQUENCE: 4
ggatccggcg cgccacgcgt ggccggcctt agtcaaaaaa ttagcctttt aattctgctg      60
taacccgtac atgcccaaaa taggggcgg gttacacaga atatataaca tcgtaggtgt     120
ctgggtgaac agtttattcc tggcatccac taaatataat ggagcccgct ttttaagctg     180
gcatccagaa aaaaaagaa tcccagcacc aaaatattgt tttcttcacc aaccatcagt     240
tcataggtcc attctcttag cgcaactaca gagaacaggg gcacaaacag gcaaaaaacg     300
ggcacaacct caatggagtg atgcaacctg cctggagtaa atgatgacac aaggcaattg     360
acccacgcat gtatctatct catttttctta caccttctat taccttctgc tctctctgat     420
ttggaaaaag ctgaaaaaaa aggttgaaac cagttccctg aaattattcc cctacttgac     480
taataagtat ataagacgg taggtattga ttgtaattct gtaaatctat ttcttaaact     540
tcttaaattc tactttttata gttagtcttt tttttagttt taaaacacca agaacttagt     600
ttcgaataaa cacacataaa caaacaaaat ggttaaggtt gccatcttag gtgcttctgg     660
tggtgtcggt caaccattat ctctattatt gaaattgtct ccatacgttt ctgaattggc     720
tttgtacgat atcagagctg ctgaaggtat tggtaaggat ttgtcccaca tcaacaccaa     780
ctcctcttgt gttggttacg acaaggattc catcgaaaac actttgtcca atgctcaagt     840
```

```
tgtcttgatt ccagctggtg ttccaagaaa gccaggtttg accagagatg atttgttcaa        900
gatgaacgct ggtatcgtta agtctttggt tactgctgtc ggtaaatttg ccccaaacgc        960
tcgtatctta gtcatctcca accctgttaa ctctttggtt ccaattgccg ttgaaacttt       1020
gaagaagatg ggtaagttca agccaggtaa cgttatgggt gtcaccaact tggatttggt       1080
cagagctgaa actttcttgg ttgactactt gatgttgaag aacccaaaga tcggtcaaga       1140
acaagacaag accaccatgc acagaaaggt caccgtcatc ggtggtcact ctggtgaaac       1200
catcattcca atcatcactg acaaatcctt ggttttccaa ttggacaagc aatacgaaca       1260
tttcatccac agagtccaat tcggtggtga cgaaattgtc aaggccaagc aaggtgccgg       1320
ttctgctacc ttgtccatgg cttttcgctgg tgccaaattt gctgaagaag tcttacgttc       1380
tttccacaac gaaaagccag aaactgaatc tttgtctgct ttcgtctact tgccaggttt       1440
gaagaacggt aagaaggctc aacaattagt cggtgacaac tccattgaat acttctcttt       1500
gccaattgtt tgagaaacg gttccgttgt tccattgac acttctgttt tggaaaaatt        1560
gtctccaaga gaagaacaat tggtcaacac tgctgtcaag gaattgagaa agaacattga       1620
aaagggtaag tctttcatct tggacagtta aggtgaattt actttaaatc ttgcatttaa       1680
ataaattttc tttttatagc tttatgactt agtttcaatt tatatactat tttaatgaca       1740
ttttcgattc attgattgaa agctttgtgt tttttcttga tgcgctattg cattgttctt       1800 gtcttttcg ccacatgtaa tatctgtagt agatacctga tacattgtgg atgctgagtg        1860 aaatttagt taataatgga ggcgctctta ataattttgg ggatattggc ttttttttt         1920 aaagtttaca aatgaatttt ttccgccagg atgggcccgc ggccgc                      1966
```

<210> SEQ ID NO 5
<211> LENGTH: 2240
<212> TYPE: DNA
<213> ORGANISM: Artificial Sequence
<220> FEATURE:
<223> OTHER INFORMATION: Synthetic construct Eno1p-SpMAE1-ENOt for expression in S. cerevisiae

<400> SEQUENCE: 5

```
ggatccggcg cgccccgcgg aaccgccaga tattcattac ttgacgcaaa agcgtttgaa         60
ataatgacga aaagaaggga agaaaaaaaa agaaaaatac cgcttctagg cgggttatct       120
actgatccga gcttccacta ggatagcacc caaacacctg catatttgga cgacctttac       180
ttacaccacc aaaaaccact ttcgcctctc ccgccctga taacgtccac taattgagcg        240
attacctgag cggtcctctt tgtttgcag catgagactt gcatactgca atcgtaagt        300 agcaacgtct caaggtcaaa actgtatgga aaccttgtca cctcacttaa ttctagctag       360
cctaccctgc aagtcaagag gtctccgtga ttcctagcca cctcaaggta tgcctctccc       420
cggaaactgt ggccttttct ggcacacatg atctccacga tttcaacata taaatagctt       480
ttgataatgg caatattaat caaatttatt ttacttcttt cttgtaacat ctctcttgta       540
atcccttatt ccttctagct attttttcata aaaaaccaag caactgctta tcaacacaca       600
aacactaaaa caaaatgggt gaattgaagg aaatcttgaa gcaacgttac catgaattgt       660
tggactggaa cgtcaaggct ccacacgttc cattgtctca aagattgaag catttcacct       720
ggtcctggtt tgcttgtacc atggccactg tggtgtcgg tttgatcatt ggttctttcc       780
cattcagatt ctacgttttg aacaccattg gtaagattgt ctacatctta caaatcttct       840
tattctcttt gtttggttct tgtatgttgt tcagattcat caaataccca tctaccatca       900
```

```
aggactcctg gaaccaccac ttggaaaaat tattcattgc tacctgtttg ctatccatct    960
ccactttcat tgacatgttg gccatctacg cttacccaga cactggtgaa tggatggtct   1020
gggttatcag aatcttatac tacatctacg ttgctgtctc tttcatctac tgtgtcatgg   1080
ctttcttcac cattttcaac aaccacgttt acaccattga aactgcttct ccagcttgga   1140
tcttaccaat tttcccacca atgatctgtg gtgtcattgc tggtgctgtc aactccactc   1200
aaccagctca ccaattgaag aacatggtta tcttcggtat cttattccaa ggtttgggtt   1260
tctgggttta cttgttgttg tttgctgtca acgttttgag attcttcacc gttggttttgg  1320 ccaagcctca agacagacca ggtatgttca tgtttgttgg tccaccagct ttctccggtt   1380
tggctttgat caacattgcc cgtggtgcta tgggttccag accatacatt ttcgtcggtg   1440
ccaattcttc tgaatacttg ggtttcgttt ccactttcat ggccattttc atctggggtt   1500
tggctgcttg gtgttactgt ttggccatgg tttctttctt ggctggtttc ttcaccagag   1560
ctccattgaa atttgcttgt ggttggtttg ctttcatctt cccaaacgtc ggtttcgtta   1620
actgtaccat tgaaattggt aagatgattg actccaaggc cttccaaatg ttcggtcaca   1680
tcatcggtgt catcctatgt atccaatgga tcttgttgat gtacttgatg gtcagagctt   1740
tcttggtcaa cgatttgtgt tacccaggta aggatgaaga tgctcaccca cctccaaagc   1800
caaacactgg tgttttgaac ccaactttcc caccagaaaa ggctccagct tctttggaaa   1860
aggttgacac ccacgttact tccactggtg gtgaatctga tcctccatct tctgaacacg   1920
aaagcgttta agagcttttg attaagcctt ctagtccaaa aaacacgttt ttttgtcatt   1980
tatttcattt tcttagaata gtttagttta ttcattttat agtcacgaat gttttatgat   2040
tctatatagg gttgcaaaca agcattttc attttatgtt aaaacaattt caggtttacc   2100
ttttattctg cttgtggtga cgcgggtatc cgcccgctct tttggtcacc catgtattta   2160
attgcataaa taattcttaa aagtggagct agtctatttc tatttacata cctctcattt   2220
ctcatttcct ccgcggccgc                                              2240
```

<210> SEQ ID NO 6
<211> LENGTH: 538
<212> TYPE: PRT
<213> ORGANISM: Artificial Sequence
<220> FEATURE:
<223> OTHER INFORMATION: Actinobacillus succinogenes phosphoenolpyruvate
      carboxykinase amino acid sequence, with EGY to DAF modification at
      pos 120 - 122.

<400> SEQUENCE: 6

```
Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
    50                  55                  60

Ser Pro Lys Asp Lys Tyr Ile Val Cys Asp Glu Thr Thr Lys Asp Thr
65                  70                  75                  80

Val Trp Trp Asn Ser Glu Ala Ala Lys Asn Asp Asn Lys Pro Met Thr
                85                  90                  95

Gln Glu Thr Trp Lys Ser Leu Arg Glu Leu Val Ala Lys Gln Leu Ser
            100                 105                 110
```

```
Gly Lys Arg Leu Phe Val Val Asp Ala Phe Cys Gly Ala Ser Glu Lys
        115                 120                 125

His Arg Ile Gly Val Arg Met Val Thr Glu Val Ala Trp Gln Ala His
130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
                180                 185                 190

Ile Thr Glu Gly Ile Gln Leu Ile Gly Gly Thr Trp Tyr Gly Gly Glu
                195                 200                 205

Met Lys Lys Gly Met Phe Ser Met Met Asn Tyr Phe Leu Pro Leu Lys
        210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
        260                 265                 270

Glu Ser Gly Val Phe Asn Phe Glu Gly Gly Cys Tyr Ala Lys Thr Ile
        275                 280                 285

Asn Leu Ser Gln Glu Asn Glu Pro Asp Ile Tyr Gly Ala Ile Arg Arg
        290                 295                 300

Asp Ala Leu Leu Glu Asn Val Val Val Arg Ala Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
                340                 345                 350

Thr Lys Val Ile Phe Leu Thr Ala Asp Ala Phe Gly Val Leu Pro Pro
        355                 360                 365

Val Ser Lys Leu Thr Pro Glu Gln Thr Glu Tyr Tyr Phe Leu Ser Gly
        370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
                420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                485                 490                 495

Thr Tyr Ala Asp Lys Ala Gln Trp Gln Val Lys Ala Glu Asp Leu Ala
                500                 505                 510

Asn Arg Phe Val Lys Asn Phe Val Lys Tyr Thr Ala Asn Pro Glu Ala
        515                 520                 525
```

```
Ala Lys Leu Val Gly Ala Gly Pro Lys Ala
    530                 535
```

<210> SEQ ID NO 7
<211> LENGTH: 1139
<212> TYPE: PRT
<213> ORGANISM: Artificial Sequence
<220> FEATURE:
<223> OTHER INFORMATION: Glycosomal Trypanosoma brucei fumarate
      reductase (FRDg) amino acid sequence lacking 3 aa C-terminal
      targeting signal.

<400> SEQUENCE: 7

```
Met Val Asp Gly Arg Ser Ser Ala Ser Ile Val Ala Val Asp Pro Glu
1               5                   10                  15

Arg Ala Ala Arg Glu Arg Asp Ala Ala Ala Arg Ala Leu Leu Gln Asp
            20                  25                  30

Ser Pro Leu His Thr Thr Met Gln Tyr Ala Thr Ser Gly Leu Glu Leu
        35                  40                  45

Thr Val Pro Tyr Ala Leu Lys Val Val Ala Ser Ala Asp Thr Phe Asp
    50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
        115                 120                 125

Cys Phe Asp Pro Ser Thr Ala Pro Val Ala Lys Ala Leu Arg Glu Ile
    130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
        195                 200                 205

Phe Gln Asn Val Phe Phe Asp Trp Gly Gly Asp Cys Arg Ala Ser Gly
    210                 215                 220

Met Asn Ala Arg Asn Thr Pro Trp Val Val Gly Ile Thr Arg Pro Pro
225                 230                 235                 240

Ser Leu Asp Met Leu Pro Asn Pro Lys Glu Ala Ser Tyr Ile Ser
                245                 250                 255

Val Ile Ser Leu Asp Asn Glu Ala Leu Ala Thr Ser Gly Asp Tyr Glu
            260                 265                 270

Asn Leu Ile Tyr Thr Ala Asp Asp Lys Pro Leu Thr Cys Thr Tyr Asp
        275                 280                 285

Trp Lys Gly Lys Glu Leu Met Lys Pro Ser Gln Ser Asn Ile Ala Gln
    290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
                325                 330                 335

Gly Trp Arg Tyr Val Arg Asp Thr Val Arg Asp Tyr Arg Val Tyr Val
```

```
                  340             345                 350
Arg Glu Asn Glu Arg Val Ala Lys Met Phe Glu Ile Ala Thr Glu Asp
                355                 360                 365
Ala Glu Met Arg Lys Arg Ile Ser Asn Thr Leu Pro Ala Arg Val
    370                 375                 380
Ile Val Val Gly Gly Gly Leu Ala Gly Leu Ser Ala Ala Ile Glu Ala
385                 390                 395                 400
Ala Gly Cys Gly Ala Gln Val Val Leu Met Glu Lys Glu Ala Lys Leu
                405                 410                 415
Gly Gly Asn Ser Ala Lys Ala Thr Ser Gly Ile Asn Gly Trp Gly Thr
                420                 425                 430
Arg Ala Gln Ala Lys Ala Ser Ile Val Asp Gly Gly Lys Tyr Phe Glu
                435                 440                 445
Arg Asp Thr Tyr Lys Ser Gly Ile Gly Gly Asn Thr Asp Pro Ala Leu
                450                 455                 460
Val Lys Thr Leu Ser Met Lys Ser Ala Asp Ala Ile Gly Trp Leu Thr
465                 470                 475                 480
Ser Leu Gly Val Pro Leu Thr Val Leu Ser Gln Leu Gly Gly His Ser
                485                 490                 495
Arg Lys Arg Thr His Arg Ala Pro Asp Lys Lys Asp Gly Thr Pro Leu
                500                 505                 510
Pro Ile Gly Phe Thr Ile Met Lys Thr Leu Glu Asp His Val Arg Gly
                515                 520                 525
Asn Leu Ser Gly Arg Ile Thr Ile Met Glu Asn Cys Ser Val Thr Ser
                530                 535                 540
Leu Leu Ser Glu Thr Lys Glu Arg Pro Asp Gly Thr Lys Gln Ile Arg
545                 550                 555                 560
Val Thr Gly Val Glu Phe Thr Gln Ala Gly Ser Gly Lys Thr Thr Ile
                565                 570                 575
Leu Ala Asp Ala Val Ile Leu Ala Thr Gly Gly Phe Ser Asn Asp Lys
                580                 585                 590
Thr Ala Asp Ser Leu Leu Arg Glu His Ala Pro His Leu Val Asn Phe
                595                 600                 605
Pro Thr Thr Asn Gly Pro Trp Ala Thr Gly Asp Gly Val Lys Leu Ala
                610                 615                 620
Gln Arg Leu Gly Ala Gln Leu Val Asp Met Asp Lys Val Gln Leu His
625                 630                 635                 640
Pro Thr Gly Leu Ile Asn Pro Lys Asp Pro Ala Asn Pro Thr Lys Phe
                645                 650                 655
Leu Gly Pro Glu Ala Leu Arg Gly Ser Gly Gly Val Leu Leu Asn Lys
                660                 665                 670
Gln Gly Lys Arg Phe Val Asn Glu Leu Asp Leu Arg Ser Val Val Ser
                675                 680                 685
Lys Ala Ile Met Glu Gln Gly Ala Glu Tyr Pro Gly Ser Gly Gly Ser
                690                 695                 700
Met Phe Ala Tyr Cys Val Leu Asn Ala Ala Gln Lys Leu Phe Gly
705                 710                 715                 720
Val Ser Ser His Glu Phe Tyr Trp Lys Lys Met Gly Leu Phe Val Lys
                725                 730                 735
Ala Asp Thr Met Arg Asp Leu Ala Ala Leu Ile Gly Cys Pro Val Glu
                740                 745                 750
Ser Val Gln Gln Thr Leu Glu Glu Tyr Glu Arg Leu Ser Ile Ser Gln
                755                 760                 765
```

Arg Ser Cys Pro Ile Thr Arg Lys Ser Val Tyr Pro Cys Val Leu Gly
                770                 775                 780

Thr Lys Gly Pro Tyr Tyr Val Ala Phe Val Thr Pro Ser Ile His Tyr
785                 790                 795                 800

Thr Met Gly Gly Cys Leu Ile Ser Pro Ser Ala Glu Ile Gln Met Lys
                805                 810                 815

Asn Thr Ser Ser Arg Ala Pro Leu Ser His Ser Asn Pro Ile Leu Gly
                820                 825                 830

Leu Phe Gly Ala Gly Glu Val Thr Gly Gly Val His Gly Gly Asn Arg
                835                 840                 845

Leu Gly Gly Asn Ser Leu Leu Glu Cys Val Val Phe Gly Arg Ile Ala
                850                 855                 860

Gly Asp Arg Ala Ser Thr Ile Leu Gln Arg Lys Ser Ser Ala Leu Ser
865                 870                 875                 880

Phe Lys Val Trp Thr Thr Val Leu Arg Glu Val Arg Glu Gly Gly
                885                 890                 895

Val Tyr Gly Ala Gly Ser Arg Val Leu Arg Phe Asn Leu Pro Gly Ala
                900                 905                 910

Leu Gln Arg Ser Gly Leu Ser Leu Gly Gln Phe Ile Ala Ile Arg Gly
                915                 920                 925

Asp Trp Asp Gly Gln Gln Leu Ile Gly Tyr Tyr Ser Pro Ile Thr Leu
                930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
                965                 970                 975

Met Lys Ala Cys Gly Gly Leu Val Ile Glu Arg Arg Leu Ser Asp Lys
                980                 985                 990

His Phe Val Phe Met Gly His Ile Ile Asn Lys Leu Cys Leu Ile Ala
                995                 1000                1005

Gly Gly Thr Gly Val Ala Pro Met Leu Gln Ile Ile Lys Ala Ala
        1010                1015                1020

Phe Met Lys Pro Phe Ile Asp Thr Leu Glu Ser Val His Leu Ile
    1025                1030                1035

Tyr Ala Ala Glu Asp Val Thr Glu Leu Thr Tyr Arg Glu Val Leu
    1040                1045                1050

Glu Glu Arg Arg Arg Glu Ser Arg Gly Lys Phe Lys Lys Thr Phe
    1055                1060                1065

Val Leu Asn Arg Pro Pro Leu Trp Thr Asp Gly Val Gly Phe
    1070                1075                1080

Ile Asp Arg Gly Ile Leu Thr Asn His Val Gln Pro Pro Ser Asp
    1085                1090                1095

Asn Leu Leu Val Ala Ile Cys Gly Pro Pro Val Met Gln Arg Ile
    1100                1105                1110

Val Lys Ala Thr Leu Lys Thr Leu Gly Tyr Asn Met Asn Leu Val
    1115                1120                1125

Arg Thr Val Asp Glu Thr Glu Pro Ser Gly Ser
    1130                1135

<210> SEQ ID NO 8
<211> LENGTH: 472
<212> TYPE: PRT
<213> ORGANISM: Artificial Sequence
<220> FEATURE:

<223> OTHER INFORMATION: Rhizopus oryzae fumarase amino acid
sequence, lacking the first 23 N-terminal amino acids.

<400> SEQUENCE: 8

```
Met Ser Ser Ala Ser Ala Leu Gln Lys Phe Arg Ala Glu Arg Asp
1               5                   10                  15

Thr Phe Gly Asp Leu Gln Val Pro Ala Asp Arg Tyr Trp Gly Ala Gln
            20                  25                  30

Thr Gln Arg Ser Leu Gln Asn Phe Asp Ile Gly Gly Pro Thr Glu Arg
        35                  40                  45

Met Pro Glu Pro Leu Ile Arg Ala Phe Gly Val Leu Lys Lys Ala Ala
    50                  55                  60

Ala Thr Val Asn Met Thr Tyr Gly Leu Asp Pro Lys Val Gly Glu Ala
65                  70                  75                  80

Ile Gln Lys Ala Ala Asp Glu Val Ile Asp Gly Ser Leu Ile Asp His
                85                  90                  95

Phe Pro Leu Val Val Trp Gln Thr Gly Ser Gly Thr Gln Thr Lys Met
            100                 105                 110

Asn Val Asn Glu Val Ile Ser Asn Arg Ala Ile Glu Leu Leu Gly Gly
        115                 120                 125

Glu Leu Gly Ser Lys Ala Pro Val His Pro Asn Asp His Val Asn Met
130                 135                 140

Ser Gln Ser Ser Asn Asp Thr Phe Pro Thr Ala Met His Val Ala Ala
145                 150                 155                 160

Val Val Glu Ile His Gly Arg Leu Ile Pro Ala Leu Thr Thr Leu Arg
                165                 170                 175

Asp Ala Leu Gln Ala Lys Ser Ala Glu Phe Glu His Ile Ile Lys Ile
            180                 185                 190

Gly Arg Thr His Leu Gln Asp Ala Thr Pro Leu Thr Leu Gly Gln Glu
        195                 200                 205

Phe Ser Gly Tyr Thr Gln Gln Leu Thr Tyr Gly Ile Ala Arg Val Gln
    210                 215                 220

Gly Thr Leu Glu Arg Leu Tyr Asn Leu Ala Gln Gly Gly Thr Ala Val
225                 230                 235                 240

Gly Thr Gly Leu Asn Thr Arg Lys Gly Phe Asp Ala Lys Val Ala Glu
                245                 250                 255

Ala Ile Ala Ser Ile Thr Gly Leu Pro Phe Lys Thr Ala Pro Asn Lys
            260                 265                 270

Phe Glu Ala Leu Ala Ala His Asp Ala Leu Val Glu Ala His Gly Ala
        275                 280                 285

Leu Asn Thr Val Ala Cys Ser Leu Met Lys Ile Ala Asn Asp Ile Arg
    290                 295                 300

Tyr Leu Gly Ser Gly Pro Arg Cys Gly Leu Gly Glu Leu Ser Leu Pro
305                 310                 315                 320

Glu Asn Glu Pro Gly Ser Ser Ile Met Pro Gly Lys Val Asn Pro Thr
                325                 330                 335

Gln Cys Glu Ala Met Thr Met Val Cys Ala Gln Val Met Gly Asn Asn
            340                 345                 350

Thr Ala Ile Ser Val Ala Gly Ser Asn Gly Gln Phe Glu Leu Asn Val
        355                 360                 365

Phe Lys Pro Val Met Ile Lys Asn Leu Ile Gln Ser Ile Arg Leu Ile
    370                 375                 380

Ser Asp Ala Ser Ile Ser Phe Thr Lys Asn Cys Val Val Gly Ile Glu
385                 390                 395                 400
```

```
Ala Asn Glu Lys Lys Ile Ser Ser Ile Met Asn Glu Ser Leu Met Leu
                405                 410                 415

Val Thr Ala Leu Asn Pro His Ile Gly Tyr Asp Lys Ala Ala Lys Cys
            420                 425                 430

Ala Lys Lys Ala His Lys Glu Gly Thr Thr Leu Lys Glu Ala Ala Leu
            435                 440                 445

Ser Leu Gly Tyr Leu Thr Ser Glu Glu Phe Asp Gln Trp Val Arg Pro
        450                 455                 460

Glu Asp Met Ile Ser Ala Lys Asp
465             470
```

<210> SEQ ID NO 9
<211> LENGTH: 340
<212> TYPE: PRT
<213> ORGANISM: Artificial Sequence
<220> FEATURE:
<223> OTHER INFORMATION: Saccharomyces cerevisiae peroxisomal malate
      dehydrogenase (Mdh3) amino acid sequence, lacking the 3 C-
      terminal peroxisomal targeting sequence (SKL).

<400> SEQUENCE: 9

```
Met Val Lys Val Ala Ile Leu Gly Ala Ser Gly Gly Val Gly Gln Pro
1               5                   10                  15

Leu Ser Leu Leu Leu Lys Leu Ser Pro Tyr Val Ser Glu Leu Ala Leu
            20                  25                  30

Tyr Asp Ile Arg Ala Ala Glu Gly Ile Gly Lys Asp Leu Ser His Ile
            35                  40                  45

Asn Thr Asn Ser Ser Cys Val Gly Tyr Asp Lys Asp Ser Ile Glu Asn
    50                  55                  60

Thr Leu Ser Asn Ala Gln Val Val Leu Ile Pro Ala Gly Val Pro Arg
65                  70                  75                  80

Lys Pro Gly Leu Thr Arg Asp Asp Leu Phe Lys Met Asn Ala Gly Ile
                85                  90                  95

Val Lys Ser Leu Val Thr Ala Val Gly Lys Phe Ala Pro Asn Ala Arg
            100                 105                 110

Ile Leu Val Ile Ser Asn Pro Val Asn Ser Leu Val Pro Ile Ala Val
            115                 120                 125

Glu Thr Leu Lys Lys Met Gly Lys Phe Lys Pro Gly Asn Val Met Gly
130                 135                 140

Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Gln Asp Lys Thr Thr
                165                 170                 175

Met His Arg Lys Val Thr Val Ile Gly Gly His Ser Gly Glu Thr Ile
            180                 185                 190

Ile Pro Ile Ile Thr Asp Lys Ser Leu Val Phe Gln Leu Asp Lys Gln
            195                 200                 205

Tyr Glu His Phe Ile His Arg Val Gln Phe Gly Gly Asp Glu Ile Val
            210                 215                 220

Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
                245                 250                 255

Pro Glu Thr Glu Ser Leu Ser Ala Phe Val Tyr Leu Pro Gly Leu Lys
            260                 265                 270
```

```
Asn Gly Lys Lys Ala Gln Gln Leu Val Gly Asp Asn Ser Ile Glu Tyr
            275                 280                 285

Phe Ser Leu Pro Ile Val Leu Arg Asn Gly Ser Val Val Ser Ile Asp
        290                 295                 300

Thr Ser Val Leu Glu Lys Leu Ser Pro Arg Glu Glu Gln Leu Val Asn
305                 310                 315                 320

Thr Ala Val Lys Glu Leu Arg Lys Asn Ile Glu Lys Gly Lys Ser Phe
                325                 330                 335

Ile Leu Asp Ser
            340

<210> SEQ ID NO 10
<211> LENGTH: 438
<212> TYPE: PRT
<213> ORGANISM: Schizosaccharomyces pombe
<220> FEATURE:
<221> NAME/KEY: MISC_FEATURE
<222> LOCATION: (1)..(438)
<223> OTHER INFORMATION: malate permease amino acid sequence

<400> SEQUENCE: 10

Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45

Gly Leu Ile Ile Gly Ser Phe Pro Phe Arg Phe Tyr Gly Leu Asn Thr
    50                  55                  60

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
        115                 120                 125

Asp Thr Gly Glu Trp Met Val Trp Val Ile Arg Ile Leu Tyr Tyr Ile
    130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
        195                 200                 205

Ile Leu Phe Gln Gly Leu Gly Phe Trp Val Tyr Leu Leu Leu Phe Ala
    210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
            260                 265                 270

Phe Val Gly Ala Asn Ser Ser Glu Tyr Leu Gly Phe Val Ser Thr Phe
```

-continued

```
            275                 280                 285
Met Ala Ile Phe Ile Trp Gly Leu Ala Ala Trp Cys Tyr Cys Leu Ala
    290                 295                 300
Met Val Ser Phe Leu Ala Gly Phe Phe Thr Arg Ala Pro Leu Lys Phe
305                 310                 315                 320
Ala Cys Gly Trp Phe Ala Phe Ile Phe Pro Asn Val Gly Phe Val Asn
                325                 330                 335
Cys Thr Ile Glu Ile Gly Lys Met Ile Asp Ser Lys Ala Phe Gln Met
            340                 345                 350
Phe Gly His Ile Ile Gly Val Ile Leu Cys Ile Gln Trp Ile Leu Leu
            355                 360                 365
Met Tyr Leu Met Val Arg Ala Phe Leu Val Asn Asp Leu Cys Tyr Pro
    370                 375                 380
Gly Lys Asp Glu Asp Ala His Pro Pro Lys Pro Asn Thr Gly Val
385                 390                 395                 400
Leu Asn Pro Thr Phe Pro Pro Glu Lys Ala Pro Ala Ser Leu Glu Lys
                405                 410                 415
Val Asp Thr His Val Thr Ser Thr Gly Gly Glu Ser Asp Pro Pro Ser
            420                 425                 430
Ser Glu His Glu Ser Val
            435
```